United States Patent
Nishino et al.

(10) Patent No.: US 8,130,909 B2
(45) Date of Patent: Mar. 6, 2012

(54) RADIOGRAPHIC IMAGING DEVICE, IMAGE PROCESSING DEVICE

(75) Inventors: Naoyuki Nishino, Kanagawa (JP); Kouichi Kitano, Kanagawa (JP); Keiji Tsubota, Kanagawa (JP); Yasunori Ohta, Kanagawa (JP); Yutaka Yoshida, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 140 days.

(21) Appl. No.: 12/546,716

(22) Filed: Aug. 25, 2009

(65) Prior Publication Data

US 2010/0054624 A1 Mar. 4, 2010

(30) Foreign Application Priority Data

Aug. 28, 2008 (JP) ................................ 2008-219933
Aug. 12, 2009 (JP) ................................ 2009-187410

(51) Int. Cl.
*H05G 1/08* (2006.01)
*H05G 1/64* (2006.01)

(52) U.S. Cl. ............. 378/91; 378/42; 378/62; 378/98.8; 250/370.09

(58) Field of Classification Search .............. 378/42, 378/62, 91, 98.8; 250/370.09
See application file for complete search history.

(56) References Cited

U.S. PATENT DOCUMENTS

| | | | | |
|---|---|---|---|---|
| 6,163,386 A * | 12/2000 | Kobayashi et al. | ............ | 358/482 |
| 6,977,988 B2 * | 12/2005 | Niwa | ............................... | 378/95 |
| 7,227,926 B2 * | 6/2007 | Kameshima et al. | ........ | 378/98.9 |
| 7,421,063 B2 * | 9/2008 | Takenaka et al. | ............. | 378/116 |
| 7,476,027 B2 * | 1/2009 | Takenaka et al. | ............. | 378/207 |
| 7,512,214 B2 * | 3/2009 | Takenaka et al. | .......... | 378/98.12 |
| 7,593,508 B2 * | 9/2009 | Tsuchiya | ...................... | 378/114 |
| 7,683,328 B2 * | 3/2010 | Tsuchiya | ................... | 250/354.1 |
| 7,810,997 B2 * | 10/2010 | Okamura | ....................... | 378/207 |
| 7,856,085 B2 * | 12/2010 | Hayashida | ....................... | 378/98 |
| 7,894,575 B2 * | 2/2011 | Tsubota et al. | ................. | 378/96 |

FOREIGN PATENT DOCUMENTS

| | | |
|---|---|---|
| JP | 2005-013272 A | 1/2005 |
| JP | 2005-046203 A | 2/2005 |

\* cited by examiner

*Primary Examiner* — Allen C. Ho
(74) *Attorney, Agent, or Firm* — SOLARIS Intellectual Property Group, PLLC

(57) ABSTRACT

There is provided a radiographic imaging device including: a radiation detector having plural sensor portions; a receiving unit that receives request data requesting radiation irradiation permission from a control device that controls a radiation source; a control unit that controls the radiation detector such that an accumulation extraction operation is repeatedly performed that extracts charge that has accumulated in each sensor portions of the radiation detector, the accumulation extraction operation being performed after a specific accumulation period has elapsed that is greater than the irradiation period of radiation; a determination unit that determines whether or not radiation irradiation of the irradiation period from the radiation source is possible within the accumulation period of the accumulation extraction operation; and a permission unit that permits radiation irradiation if the determination unit has determined that irradiation is possible, and otherwise that permits radiographic image after starting the accumulation period of the next accumulation extraction operation.

9 Claims, 10 Drawing Sheets

RADIOGRAPHIC IMAGING DEVICE, IMAGE PROCESSING DEVICE

CROSS-REFERENCE TO RELATED APPLICATION

This application is based on and claims priority under 35 USC 119 from Japanese Patent Application No. 2008-219933 filed on Aug. 28, 2008 and Japanese Patent Application No. 2009-187410 filed on Aug. 12, 2009, the disclosures of which are incorporated by reference herein.

BACKGROUND

1. Technical Field

The present invention relates to a radiographic imaging device and to an image processing device.

2. Related Art

Recently radiation detectors of FPD's (Flat Panel Detectors) etc. that can directly convert radiation into digital data have been put into practice, the FPD's having a radiation sensitive layer disposed on a TFT (Thin Film Transistor) active matrix substrate. Portable radiographic imaging devices (referred to below as "electronic cassettes") have also recently been put into practice using such FPD's or the like, the portable imaging devices generating image data representing radiographic images of radiation irradiated thereon, and storing the generated image data.

However, in such FPD's, charge is generated and accumulated in each pixel even in a state in which X-rays are not irradiated, due to dark current etc. Consequently, an accumulation extraction operation is performed repeatedly in the electronic cassette during standby to extract and remove any charge accumulated in each of the pixels of the FPD. If this accumulation extraction operation is stopped midway then a line aberration is generated in the radiographic image at the position at which the extraction operation of the reset mode was stopped, with a reduction in image quality. Therefore, in order to suppress such reduction in image quality it is necessary to wait until one frame's worth the accumulation extraction operation has been completed, with this sometimes generating a time lag till commencement of imaging.

As a technique to shorten such a time lag, a technique is described in Japanese Patent Application Laid-Open (JP-A) No. 2005-13272 in which synchronization of the accumulation extraction operation and X-ray generation timing becomes unnecessary by notifying the drive state (accumulation extraction operation) of a FPD to the person who is doing the imaging.

Also, in JP-A No. 2005-46203, by instructing X-ray imaging preparation X-ray generation preparation is performed to the X-ray source, and imaging preparation is performed in the FPD, with charge accumulation commenced a specific duration after completion of imaging preparation. When imaging is instructed within the specific duration, X-rays are irradiated from the X-ray source, and charge accumulation is ended when a specific duration has passed from commencing charge accumulation, and charge extraction is performed from each of the pixels of the FPD.

However, in the techniques of JP-A No. 2005-13272 and JP-A No. 2005-46203 suffer from the problem that the imaging timing is limited, and there are occasions when a radiographic image cannot be captured at a specific timing.

Namely, in the technique of JP-A No. 2005-13272, imaging can only be performed at a timing in accordance with the notified drive state of the FPD, and the imaging timing is limited.

In the technique of JP-A No. 2005-46203, imaging must be instructed and X-rays irradiated from the X-ray source from commencing charge accumulation of the FPD until a specific duration has elapsed, and if the specific duration is exceeded then X-ray imaging preparation must be started over again, limiting the imaging timing.

SUMMARY

The present invention is made in consideration of the above problems and an objective thereof is to provide a radiographic imaging device that can capture radiographic images at a specific timing while also shortening the time lag, and an image processing device of the same.

In order to achieve the above objective, a first aspect of the present invention provides a radiographic imaging device including:

a radiation detector that has a plurality of sensor portions that accumulate charge generated when radiation is irradiated thereon when capturing a radiographic image;

a receiving unit that receives request data requesting radiation irradiation permission from a control device that controls a radiation source for radiation irradiation when capturing a radiographic image;

a control unit that controls the radiation detector such that an accumulation extraction operation is repeatedly performed that extracts charge that has accumulated in each of the respective sensor portions of the radiation detector, the accumulation extraction operation being performed after a specific accumulation period has elapsed that is greater than the irradiation period of radiation irradiation from the radiation source when capturing a radiographic image;

a determination unit that, when the request data is received by the receiving unit, determines whether or not radiation irradiation of the irradiation period from the radiation source is possible within the accumulation period of the accumulation extraction operation currently being carried out under control of the control unit; and a permission unit that permits radiation irradiation if the determination unit has determined that irradiation is possible, and that permits radiographic image after starting the accumulation period of the next accumulation extraction operation if the determination unit has determined that radiation is not possible.

According to the present invention, the radiation detector has plural sensor portions that accumulate charge generated when radiation is irradiated thereon. When capturing a radiographic image request data requesting radiation irradiation permission, from a control device that controls a radiation source for radiation irradiation, is also received by a receiving unit.

In the present invention, the radiation detector is controlled by a control unit such that an accumulation extraction operation is repeatedly performed that extracts charge that has accumulated in each of the respective sensor portions of the radiation detector, the accumulation extraction operation being performed after a specific accumulation period has elapsed that is greater than the irradiation period of radiation irradiation from the radiation source when capturing a radiographic image.

In the present invention, when the request data is received by the receiving unit, the determination is made by the determination unit as to whether or not radiation irradiation of the irradiation period from the radiation source is possible within the accumulation period of the accumulation extraction operation currently being carried out under control of the control unit. If the determination unit has determined that irradiation is possible then permission for radiation irradiation is given by the permission unit, and if the determination unit has determined that irradiation is not possible permission for radiation irradiation is given by the permission unit after starting the accumulation period of the next accumulation extraction operation.

In this manner, according to the present invention a radiographic image can be captured with shortened time lag, since the radiation detector is controlled such that an accumulation extraction operation is repeatedly performed that extracts charge that has accumulated in each of the respective sensor portions of the radiation detector, the accumulation extraction operation being performed after a specific accumulation period has elapsed that is greater than the irradiation period of radiation irradiation from the radiation source when capturing a radiographic image, and when a request data requesting radiation irradiation permission is received, determination is made as to whether or not irradiation is possible of the irradiation period from the radiation source within the accumulation period of the accumulation extraction operation currently being carried out, and permission for radiation irradiation is given if irradiation is possible. If determination is that irradiation is not possible, permission for radiation irradiation is given after starting the accumulation period of the next accumulation extraction operation, therefore the image capture timing is not limited, and radiographic image capture can be made at a desired timing.

In the present invention, the determination unit may determine irradiation to be possible when an interval until completion of the accumulation period of the accumulation extraction operation currently being carried out is the same as or greater than a summed duration of the irradiation period plus a specific irradiation delay period, and may determine irradiation not to be possible when the interval until completion is shorter than the summed duration.

The irradiation delay period is preferably equivalent to an interval from when radiation irradiation permission is given to when radiation is actually irradiated.

The receiving unit may also be able to communicate with the control device by wired communication or wireless communication. The control unit may control the radiation detector such that the accumulation extraction operation is repeatedly performed when the receiving unit is performing wireless communication, and control the radiation detector so that an extraction operation is repeatedly performed that extracts the charge that has accumulated in each of the respective sensor portions of the radiation detector when the receiving unit is performing wired communication. The permission unit may give permission for radiation irradiation at a timing when the extraction operation currently being carried out is completed when the receiving unit is performing wired communication.

Preferably the receiving unit is able to communicate with the control device by wired communication or wireless communication, and the control unit sets the accumulation period relatively longer when the receiving unit is performing wireless communication than when performing wired communication.

The radiographic imaging device may be further equipped with an image processing unit that performs image processing that corrects image data representing a radiographic image that is based on the charge amount extracted from each of the sensor portions of the radiation detector in one of the accumulation extraction operations when radiation has been irradiated onto the radiation detector, with data representing noise based on the charge amount extracted from each of the sensor portions of the radiation detector in one of the accumulation extraction operations when radiation has not yet been irradiated onto the radiation detector.

The image processing unit may perform image processing that corrects image data representing a radiographic image with data representing noise based on the charge amounts extracted in the accumulation extraction operation performed just after capturing the radiographic image.

The image processing unit may perform image processing that corrects image data representing a radiographic image with data representing noise based on the charge amounts extracted in one of the accumulation extraction operations performed before capturing the radiographic image.

The radiographic imaging device may further include a display unit that displays a radiographic image represented by image data prior to performing image processing by the image processing unit.

A second aspect of the present invention provides an image processing device including:

a plurality of sensor portions that accumulate charge generated when radiation is irradiated thereon when capturing a radiographic image; and an image processing unit that performs image processing that corrects image data representing a radiographic image based on charge amounts extracted from each of the sensor portions of a radiation detector in an accumulation extraction operation when radiation has been irradiated onto the radiation detector, the radiation detector controlled such that the accumulation extraction operation is repeatedly performed to extract charge that has accumulated in each of the respective sensor portions of the radiation detector after a specific accumulation period has elapsed that is greater than the irradiation period for radiation irradiation from the radiation source when capturing a radiographic image, with data representing noise based on the charge amount extracted from each of the sensor portions of the radiation detector in one of the accumulation extraction operations when radiation has not yet been irradiated onto the radiation detector.

According to the second aspect of the present invention, noise generated by dark current or the like can be removed from image data representing a radiographic image by performing image processing that corrects image data representing a radiographic image based on the charge amount extracted from each of the sensor portions of a radiation detector in one of the accumulation extraction operations when radiation has been irradiated onto the radiation detector controlled such that the above accumulation extraction operation is repeatedly performed, with data representing noise based on the charge amount extracted from each of the sensor portions of the radiation detector in one of the accumulation extraction operations when radiation has not yet been irradiated onto the radiation detector.

According to the present invention the excellent effect is obtained that radiographic images can be obtained with a desired timing while shortening the time lag.

BRIEF DESCRIPTION OF THE DRAWINGS

Exemplary embodiments of the present invention will be described in detail based on the following figures, wherein.

DETAILED DESCRIPTION

Explanation will be given below of details of the best mode of implementing the present invention, with reference to the drawings.

First Exemplary Embodiment

Explanation will first be given of a configuration of a radiology information system 10 according to a first exemplary embodiment.

Figure 1:
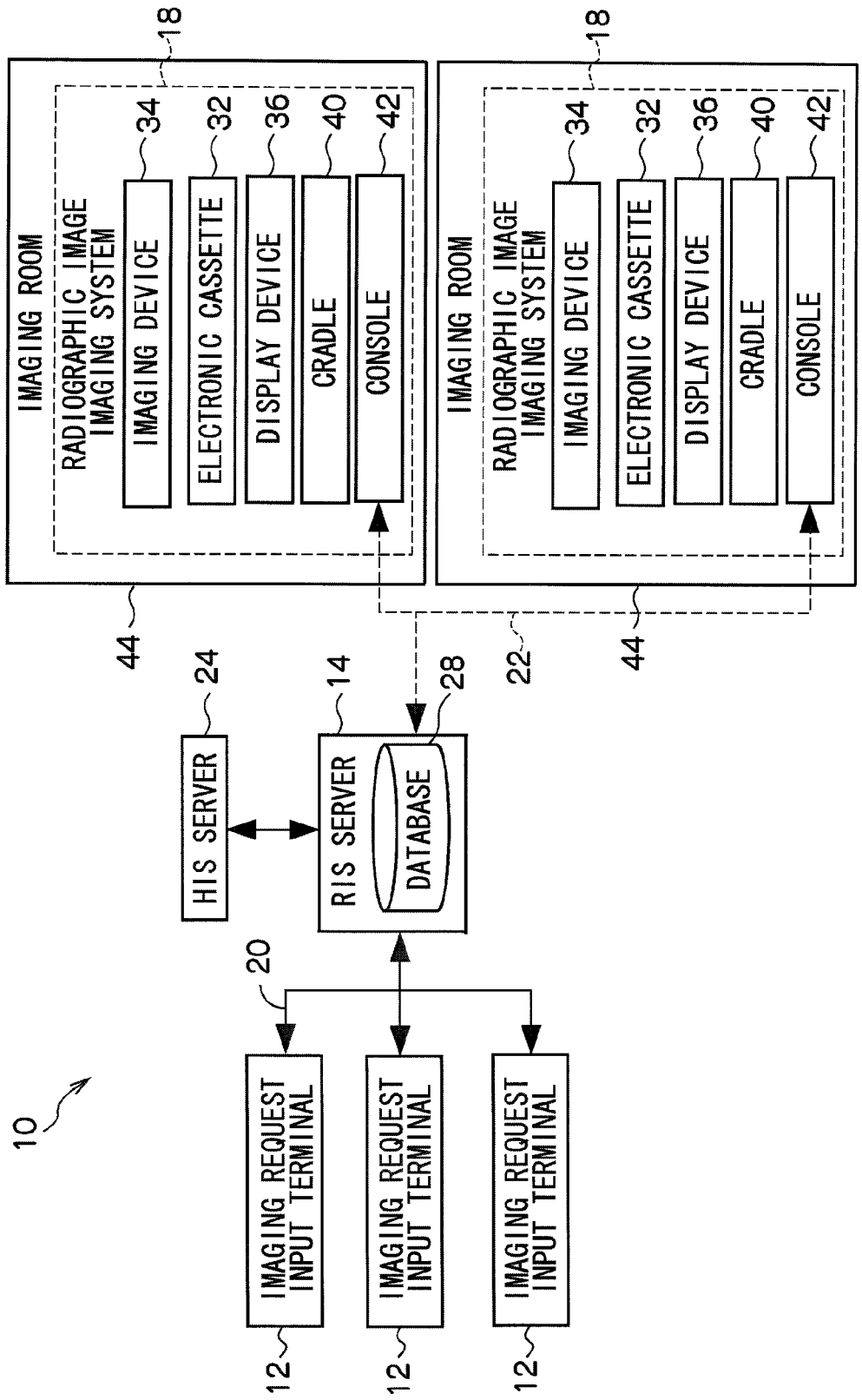
FIG. 1 is a block diagram showing a configuration of a radiology information system according to an exemplary embodiment.

FIG. 1 shows a block diagram of each essential element of the configuration of a radiology information system 10 (referred to below as RIS 10, RIS: Radiology Information System) according to the present exemplary embodiment.

The RIS 10 is a system for performing information management in a radiology department, such as management of consultation appointments, consultation records etc., and the RIS 10 configures part of an HIS (Hospital Information System).

The RIS 10 is configured including: plural imaging request input terminals 12 (referred to below as input terminals 12); an RIS server 14; and plural radiographic imaging systems 18 (referred to below as imaging systems 18).

The RIS server 14 is for overall management of the RIS 10, and configuration is made such that each of the input terminals 12 and the imaging systems 18 can mutually communicate with one another via LAN (Local Area Network) cables 20 or wireless LAN 22. The RIS server 14 is connected to an HIS server 24 that performs overall management of the HIS.

The input terminal 12 is for input and viewing of consultation information and facility reservations by a surgeon 26 (see FIG. 2) or radiologist, and imaging requests for radiographic images (imaging reservations) are also input via the input terminal 12. Each of the input terminals 12 is configured from a PC with monitor, and is connected to the RIS server 14 via a LAN to enable mutual communication therewith.

The RIS server 14 receives imaging requests from each of the input terminals 12, manages the imaging schedule of radiographic images in the imaging systems 18, and is configured with a database 28.

The database 28 is configured with: attribute information of patients 30 (see FIG. 2) (name, gender, date of birth, age, blood group, ID no. etc.); information related to the patient 30, such as illness history, consultation history, previously imaged radiographic images etc.; information related to the electronic cassettes 32, such as identification number of the electronic cassette 32 of the imaging system 18, format, size, position thereon possible for imaging (contents of imaging requests that can be responded to), date of first use, number of times of use etc.; and environmental information including the environment for radiographic imaging using the electronic cassette 32, namely the usage environment of the electronic cassette 32 (as an example, the operation room or imaging room set up specifically for capturing radiographic images).

The imaging systems 18 perform imaging of radiographic images under operation of the surgeon 26 or radiologist, according to instructions from the RIS server 14. The imaging system 18 is equipped with: an imaging device 34 that irradiates X-rays onto an imaging subject with a radiation amount in accordance with imaging conditions; an electronic cassette 32, internally installed with a radiation detector 60 (see FIG. 3) for detecting X-rays that have passed through the patient 30 and converting the X-rays into radiographic image data; a display device 36 for displaying radiographic images based on the X-rays detected by the radiation detector 60; a cradle 40 for charging a battery internally housed in the electronic cassette 32; and a console 42 for controlling the electronic cassette 32, the imaging device 34, the display device 36 and the cradle 40.

Figure 2:
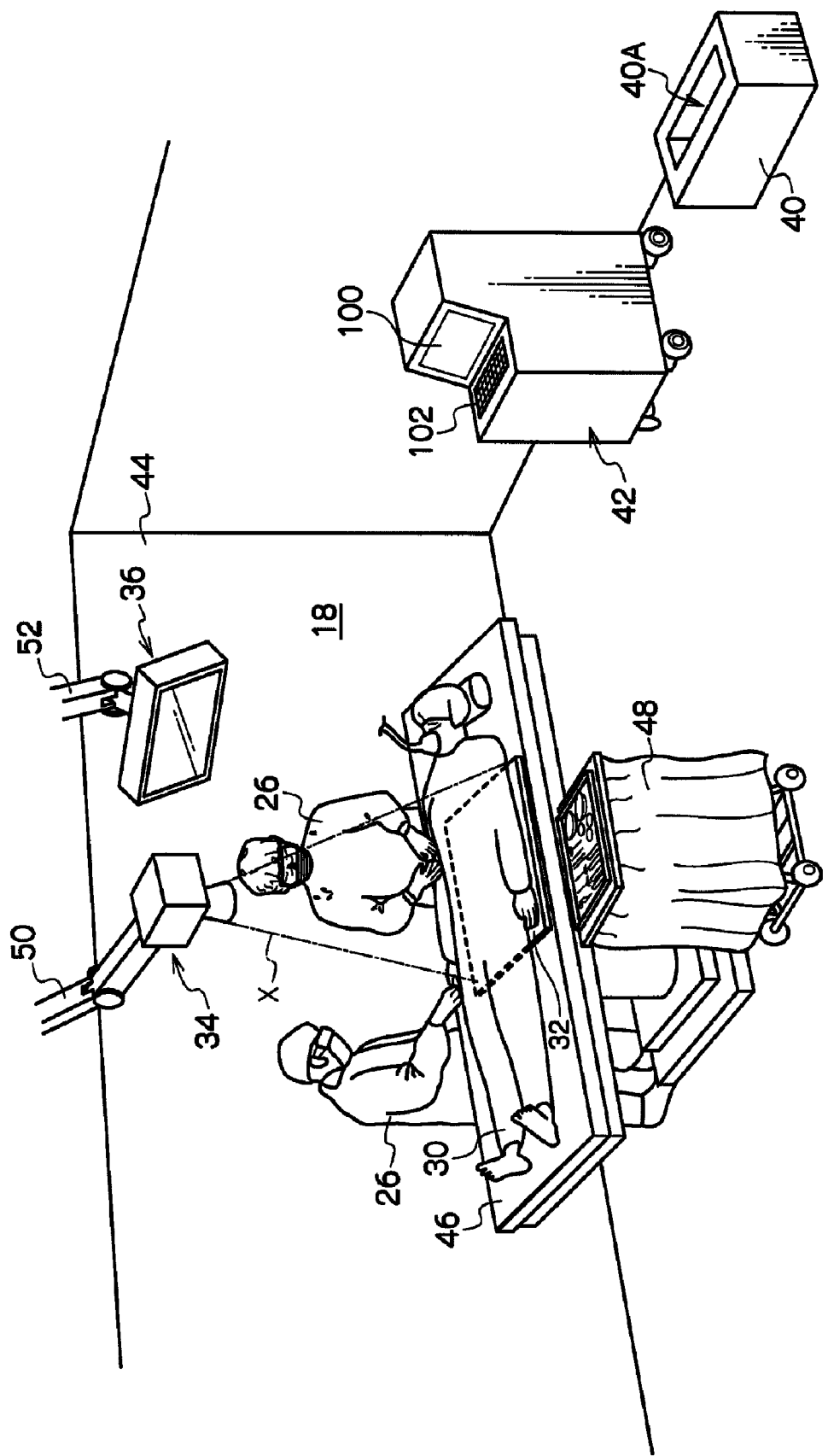
FIG. 2 is a diagram showing an arrangement of an operation room in which a radiographic imaging system according to an exemplary embodiment has been disposed.

FIG. 2 shows an example of a layout of the imaging system 18 according to the present exemplary embodiment, showing the arrangement of the imaging system 18 disposed in an operation room 44, serving as an imaging room. In the imaging system 18 of the present exemplary embodiment, transmission and receipt of various data is performed via wired communication with the imaging device 34 and the display device 36 respectively connected to the console 42 by cables, however, the cables linking each of the functional devices are omitted in FIG. 2. Transmission and receipt of various data is performed via wireless communication between the electronic cassette 32 and the console 42.

In addition to the imaging systems 18, an operating table 46, for laying out the patient 30 thereon, is also disposed in the operation room 44 of FIG. 2, together with an instrument table 48, disposed at the side of the operating table 46 and on which various instruments for use in surgery by the surgeon 26 are placed. Various instruments required for surgery are placed around the operating table 46, such as an anesthetic machine, a respirator, an electrocardiographic monitor, a blood pressure monitor, etc. (these instruments are omitted in FIG. 2).

The imaging device 34 is connected to a universal arm 50, so as to be movable to the desired position according to the imaging position on the patient 30, and so as to be able to be placed on standby in a position out of the way of the surgeon 26 performing surgery. The display device 36 is, in the same manner, connected to a universal arm 52, so as to be movable to a position when the surgeon 26 can readily check the captured radiographic images.

An accommodating portion 40A capable of housing the electronic cassette 32 is formed in the cradle 40.

When on standby, the electronic cassette 32 is accommodated in the accommodating portion 40A of the cradle 40, and recharging is carried out of the housed battery, when capturing a radiographic image the electronic cassette 32 is removed from the cradle 40 and placed at the imaging position of the patient 30.

It should be noted that the electronic cassette 32 is not limited to use within the operation room 44, and, for example, application can be made thereof to examinations and rounds in the hospital.

Figure 3:
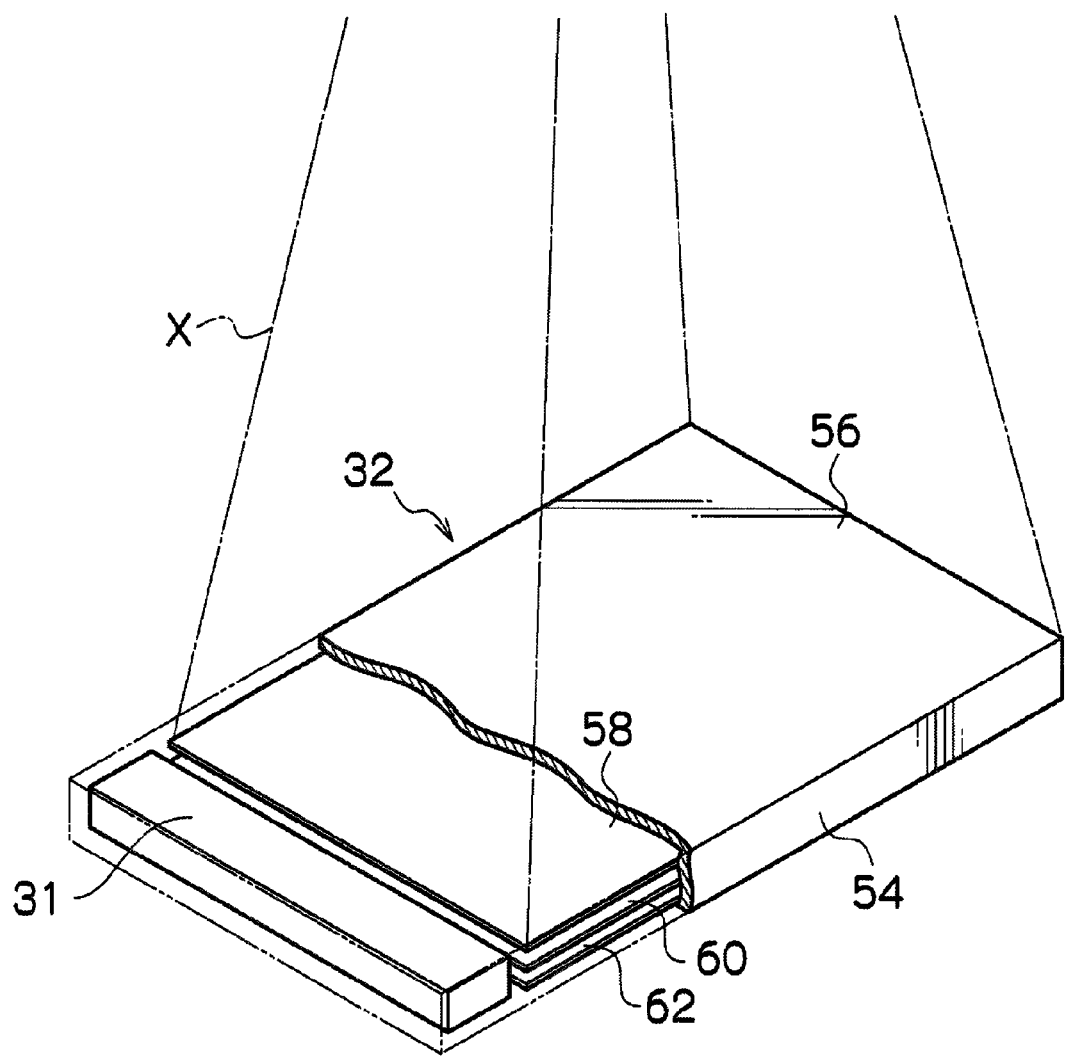
FIG. 3 is a cut-away perspective view showing the internal configuration of an electronic cassette according to an exemplary embodiment.

FIG. 3 shows the internal configuration of the electronic cassette 32 according to the first exemplary embodiment.

As shown in FIG. 3, the electronic cassette 32 is equipped with a case 54 made from a material through which X-rays can pass and configuring a waterproof, tightly sealed structure. There is a chance that the electronic cassette 32 will get adhered to by blood fluids and other germs during use in the operation room 44 or the like. Since the electronic cassette 32 is of a waterproof, tightly sealed structure, each single electronic cassette 32 can be reused repeatedly by sterilization cleaning as required.

Disposed within the case 54 (see FIG. 3), in sequence from an irradiation face 56 side of the case 54 onto which X-rays are irradiated, are: a grid 58 that removes X-rays scattered by the patient 30; a radiation detector 60 that detects X-rays that have passed through the patient 30; and a lead plate 62 that absorbs back scattered X-rays. Note that the irradiation face 56 of the case 54 may also be configured as the grid 58.

A case 31 is disposed inside the case 54 at one end, the case 31 housing electrical circuits including a microcomputer and a rechargeable battery that can be recharged. The radiation detector 60 and the electrical circuits are operated by electrical power supplied from the rechargeable battery disposed in the case 31. Preferably a lead plate or the like is disposed on the irradiation face 56 side of the case 31 in order to avoid damage to the various circuits housed within the case 31 accompanying irradiation of X-rays.

Figure 4:
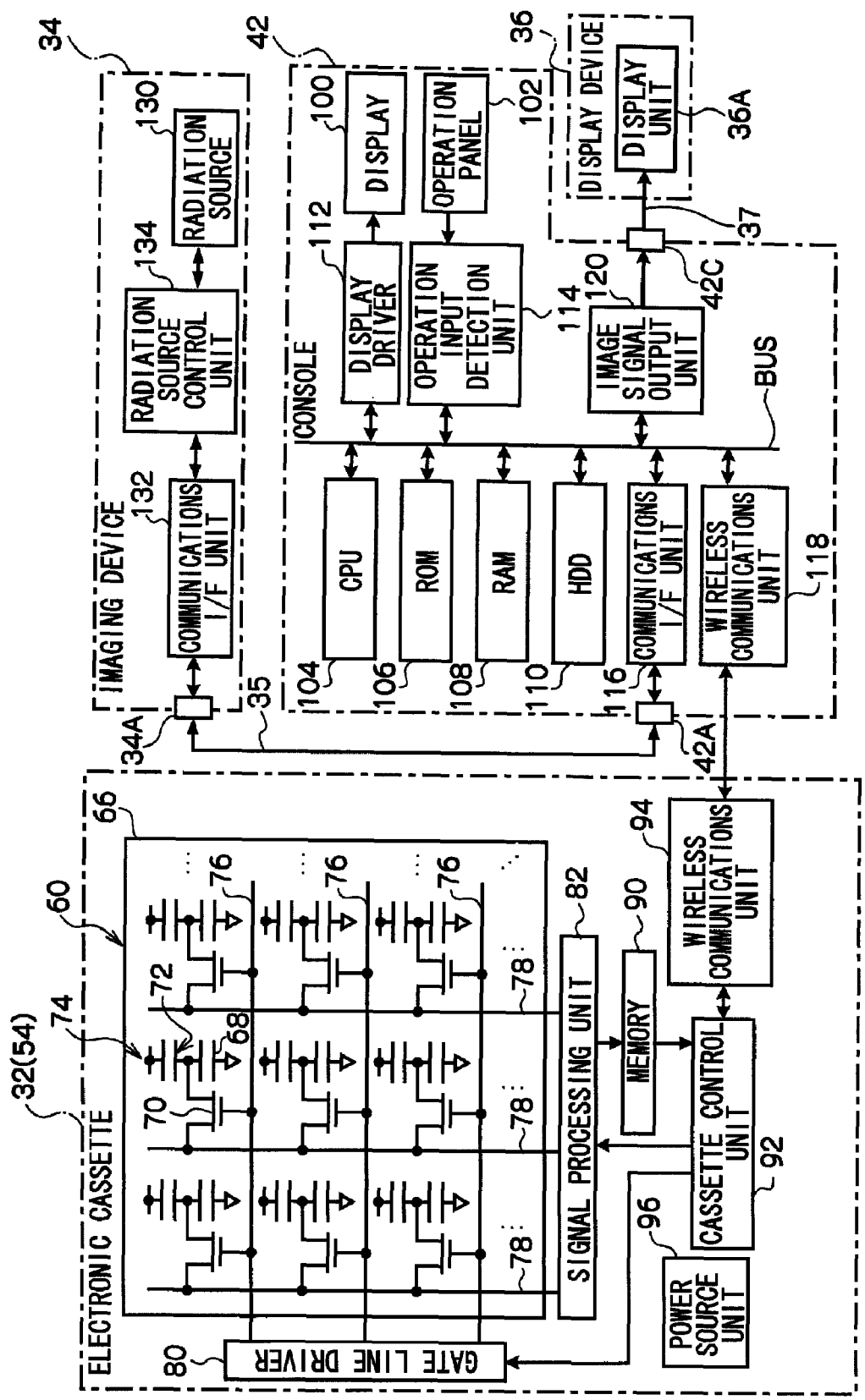
FIG. 4 is a block diagram showing a detailed configuration of a radiographic imaging system according to a first exemplary embodiment.

FIG. 4 shows a block diagram with a detailed configuration of the imaging system 18 according to the first exemplary embodiment.

A connection terminal 34A is provided to the imaging device 34 for communicating with the console 42. A connection terminal 42A is provided to the console 42 for communicating with the imaging device 34, and a connection terminal 42C is also provided to the console 42 for outputting an image signal to the display device 36.

The imaging device 34 is connected to the console 42 via a communications cable 35, and the display device 36 is connected to the console 42 via a display cable 37.

The radiation detector 60 internally housed in the electronic cassette 32 is configured with a photoelectric conversion layer layered onto a TFT active matrix substrate 66, the photoelectric conversion layer absorbing X-rays and converting X-rays into charge. The photoelectric conversion layer is formed with, for example, selenium as a main component thereof (for example contained at a proportion of 50% or above) using non-crystalline a-Se (amorphous selenium). When X-rays are irradiated onto the photoelectric conversion layer the photoelectric conversion layer converts irradiated X-rays into charge by internally generating charge (electron-hole pairs) of an amount of electric charge in accordance with the amount of irradiated radiation. It should be noted that indirect conversion into charge may be made in the radiation detector 60 using a fluorescent material and photoelectric conversion element (photodiode) in place of the direct X-ray-charge converting material, like amorphous selenium, that directly converts X-rays into charge. Gadolinium oxysulfide compounds (GOS) and cesium iodide (CsI) are well known as fluorescent materials. In such cases X-ray-light conversion is performed by the fluorescent material and light-charge conversion is performed using the photodiode photoelectric conversion element.

Plural individual pixel portions 74 are disposed in a matrix shape on the TFT active matrix substrate 66. Each of the pixel portions 74 is provided with a storage capacitor 68 for accumulating charge generated in the photoelectric conversion layer, and a TFT 70 for extracting the charge accumulated in the storage capacitor 68 (in FIG. 4 an photoelectric conversion layer corresponding to individual pixel portions 74 is shown pictorially as photoelectric conversion portions 72). The charge generated in the photoelectric conversion layer, by irradiation of the electronic cassette 32 with X-rays, is accumulated in the respective storage capacitor 68 of the individual pixel portions 74. In this manner, the image data carried in the X-rays irradiated onto the electronic cassette 32 is converted into charge data, and held in the radiation detector 60.

The TFT active matrix substrate 66 is provided with plural gate lines 76 extending along a fixed direction (row direction) for switching on and off the TFT 70 of the individual pixel portions 74, and is provided with plural data lines 78 extending in a direction perpendicular to the gate lines 76 (column direction) for extracting accumulated charge from the storage capacitors 68 through the TFT's 70 that are switched on. Individual gate lines 76 are connected to a gate line driver 80, and individual data lines 78 are connected to a signal processing unit 82. The TFT's 70 of the pixel portions 74 are switched on in sequence of single row units by a signal supplied from the gate line driver 80 through the gate lines 76, and the charge that has been accumulated in the storage capacitor 68 of the pixel portions 74 for which the TFT 70 is on, is transmitted as a charge signal through the data lines 78 and input to the signal processing unit 82. The charge that has been accumulated in the storage capacitors 68 of individual pixel portions 74 is consequently extracted in sequence in single row units.

Figure 5:
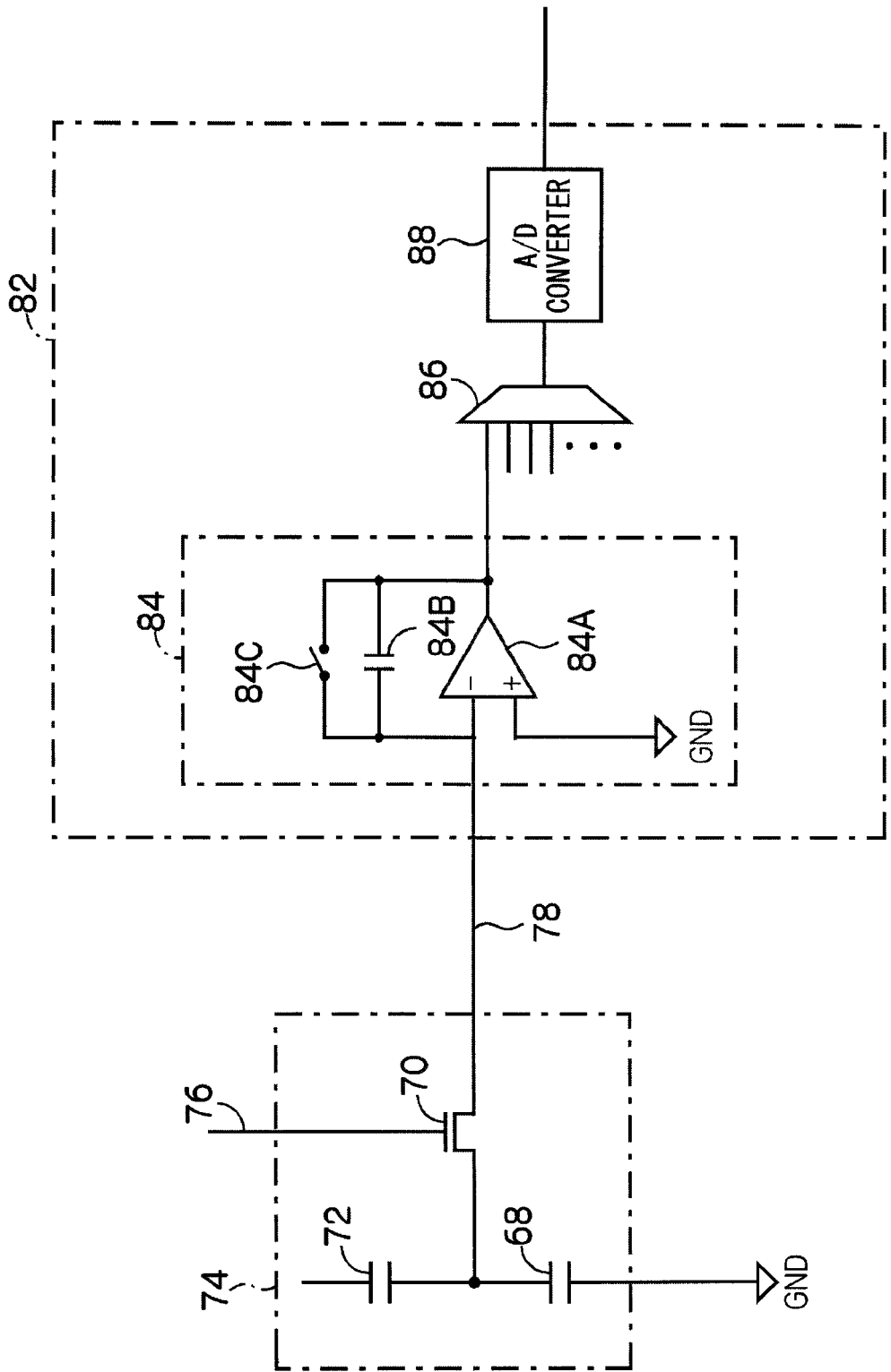
FIG. 5 is an equivalent circuit diagram focusing on a single pixel portion of a radiation detector according to an exemplary embodiment.

FIG. 5 shows an equivalent circuit diagram focusing on a single pixel portion of the radiation detector 60 according to the present exemplary embodiment.

As shown in FIG. 5, the source of the TFT 70 is connected to the data line 78, and the data line 78 is connected to the signal processing unit 82. The drain of the TFT 70 is connected to the storage capacitor 68 and to the photoelectric conversion portion 72, and the gate of the TFT 70 is connected to the gate line 76.

The signal processing unit 82 is equipped with a sample-and-hold circuit 84 for each of the individual data lines 78. The charge signal transmitted through the data line 78 is held in the sample-and-hold circuit 84. The sample-and-hold circuit 84 is configured to include an operational amplifier 84A and a condenser 84B, and converts the charge signal into an analogue voltage. In the sample-and-hold circuit 84 a switch 84C is provided for shorting both electrodes of the condenser 84B, as a reset circuit to discharge charge accumulated in the condenser 84B.

A multiplexer 86 and an A/D convertor 88 are connected in sequence to the output side of the sample-and-hold circuit 84, and the charge signals held in the individual sample-and-hold circuits 84 are converted into analogue voltages and input in sequence (serially) to the multiplexer 86, and converted into digital image data by the A/D convertor 88.

A memory 90 is connected to the signal processing unit 82 (see FIG. 4), and image data output from the A/D convertor 88 of the signal processing unit 82 is stored in sequence in the memory 90. The memory 90 has a storage capacity capable of storing image data representing radiographic images from a specific number of frames, and each time one line of charge is extracted the one line's worth of image data is stored in sequence in the memory 90.

The memory 90 is connected to a cassette control unit 92 that controls the overall operation of the electronic cassettes 32. The cassette control unit 92 is realized by a microcomputer. A wireless communications unit 94 is connected to the cassette control unit 92. The wireless communications unit 94 conforms to a wireless LAN specification, as typified by IEEE (Institute of Electrical and Electronics Engineers) 802.11a/b/g etc., and controls transmission of various data to external devices by wireless communication. The cassette control unit 92 is capable of wireless communication with the console 42 via the wireless communications unit 94, and capable of transmitting and receiving various data to and from the console 42. The cassette control unit 92 stores imaging control data received from the console 42, described later, and commences extracting charge based on this data.

A power source unit 96 is provided to the electronic cassette 32, and power supplied from the power source unit 96 operates the various circuits and elements described above (the gate line driver 80, the signal processing unit 82, the memory 90, the wireless communications unit 94, and the microcomputer functioning as the cassette control unit 92). The power source unit 96 internally houses a battery (rechargeable battery capable of recharging) so that the portability of the electronic cassette 32 is not compromised, and power is supplied from the charged battery to various circuits and elements.

The console 42 is configured as a server computer, equipped with a display 100 on which an operation menu and captured radiographic images etc. are displayed, and an operation panel 102 configured including plural keys through which various data and operation instructions are input.

The console 42 according to the present exemplary embodiment is equipped with: a CPU 104 that controls the operation of the device as a whole; a ROM 106 in which various programs etc., including a control program, are stored in advance; a RAM 108 that temporarily stores various data; a HDD 110 that stores and holds various data; a display driver 112 that controls the display of various data on the display 100; an operation input detection unit 114 that detects the operational state of the operation panel 102; a communications interface (I/F) unit 116, connected to the connection terminal 42A and transmitting and receiving various data to and from the imaging device 34 via the connection terminal 34A and the communications cable 35, such as later described radiation exposure conditions and status information of the imaging device 34 etc.; a wireless communications unit 118 that transmits and receives various data, such as imaging control data and image data, to and from the electronic cassette 32 by wireless communication; and an image signal output unit 120 that is connected to the connection terminal 42C and outputs an image signal to the display device 36 via the connection terminal 42C and the communications cable 37.

The CPU 104, the ROM 106, the RAM 108, the HDD 110, the display driver 112, the operation input detection unit 114, the communications I/F unit 116, the wireless communications unit 118, and the image signal output unit 120 are mutually connected together by a system bus BUS. Consequently, the CPU 104 can access the ROM 106, the RAM 108 and the HDD 110, and the CPU 104 can control display of various data on the display 100 via the display driver 112, can control transmitting and receiving of various data to and from the imaging device 34 via the communications I/F unit 116, and can control the display of images on the display device 36 via the image signal output unit 120. The CPU 104 can also ascertain via the operation input detection unit 114 the operational state of the operation panel 102 due to a user.

The imaging device 34 is equipped with: a radiation source 130 that outputs X-rays; a communications I/F unit 132 that transmits and receives various data, such as radiation exposure conditions and status information of the imaging device 34, to and from the console 42; and a radiation source control unit 134 that controls the radiation source 130 based on received radiation exposure conditions. The radiation source control unit 134 is also realized by a microcomputer, stores received radiation exposure conditions, and causes X-rays to be irradiated from the radiation source 130 according to the stored radiation exposure conditions.

The display device 36 is equipped with a display unit 36A that displays images representing a received image signal.

A visual display using an LCD (Liquid Crystal Display) is used as the display unit 36A and as the display 100 in the first exemplary embodiment, however there is no limitation thereto, and visual displays using other displays, such as an organic EL display, a CRT display etc., may be used as the display unit 36A and the display 100.

Simple explanation will next be given of the overall operation of the RIS 10 in the first exemplary embodiment.

The input terminal 12 (as shown in FIG. 1) receives imaging requests, including environment information, from a surgeon 26 or radiologist. The imaging requests instruct the usage environment of the electronic cassette 32, the date and time of imaging and the imaging conditions (imaging position, angle and no. of frames, tube voltage, tube current and irradiation period for X-ray irradiation, and the size and sensitivity of the electronic cassette 32, etc.)

The input terminal 12 notifies the RIS server 14 of the contents of the received imaging request. The RIS server 14 stores the contents of the radiographic image notified by the input terminal 12 in the database 28.

The console 42 acquires, by accessing the RIS server 14, the contents of the imaging request and the environment information assigned thereto from the RIS server 14, and displays the contents of the imaging request on the display 100 (see FIG. 2 and FIG. 4).

The surgeon 26 or radiologist commences capturing the radiographic image based on the contents of the radiographic image displayed on the display 100.

For example, as shown in FIG. 2, when a radiographic image is to be taken of an affected part of a patient 30 lying on the operating table 46, the surgeon 26 or radiologist disposes the electronic cassette 32 between the operating table 46 and the patient 30 according to the imaging position and angle, with the imaging device 34 disposed above the affected portion. The surgeon 26 or radiologist then performs radiation exposure condition instruction operation on the operation panel 102 of the console 42 according to the imaging position on the patient 30 and the imaging conditions, specifying the radiation exposure conditions of the tube voltage, tube current, and irradiation period etc. for X-ray irradiation. When the surgeon 26 or radiologist has completed radiation exposure preparation in the imaging device 34, imaging instruction operation is performed with respect to the operation panel 102 of the console 42 to instruct imaging.

Explanation will next be given of details of the operation of the imaging system 18 according to the first exemplary embodiment.

Figure 6:
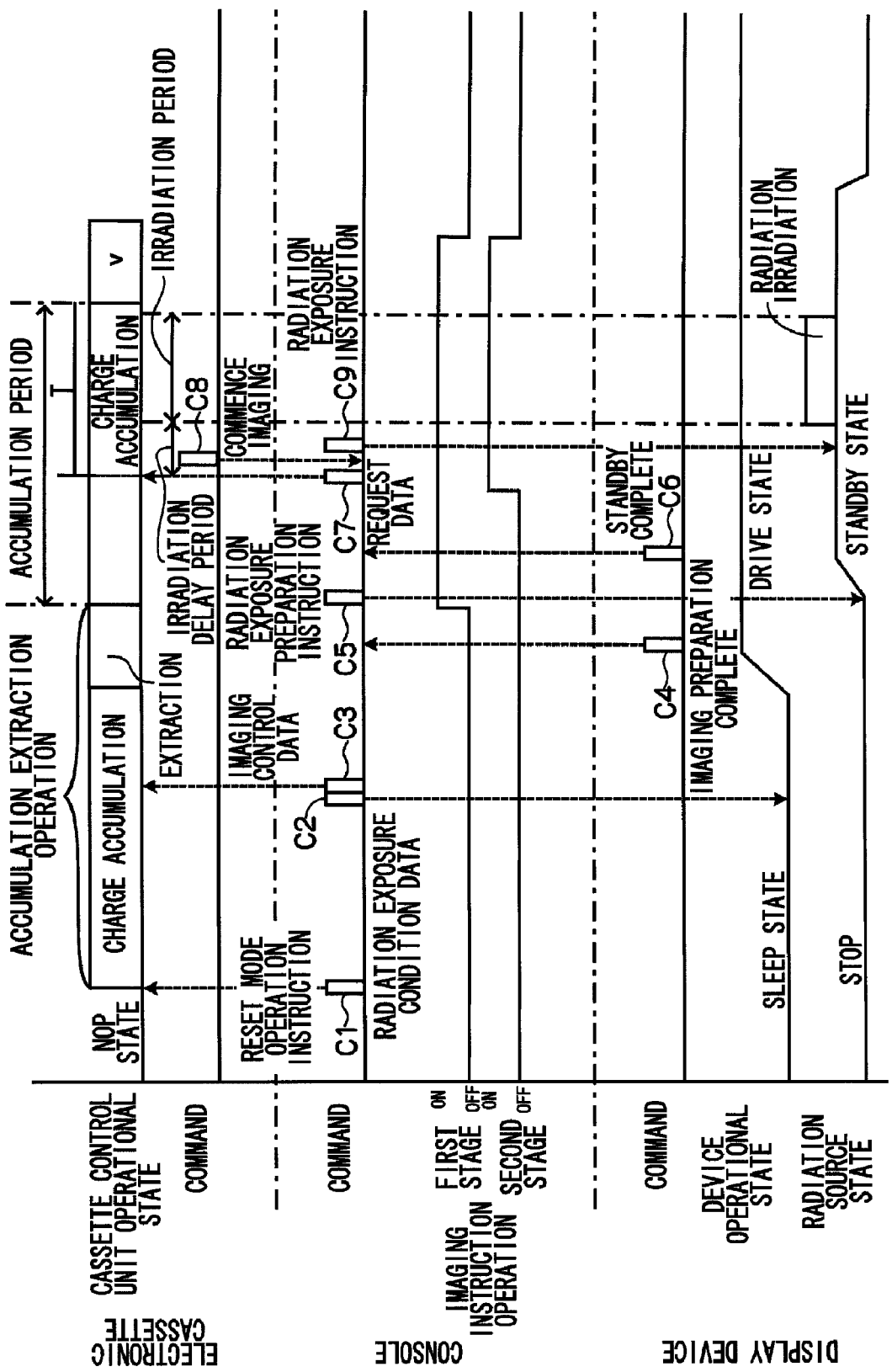
FIG. 6 is a timing chart showing the operation flow when capturing a radiographic image according to the first exemplary embodiment.

FIG. 6 shows a timing chart showing the operation flow when capturing a radiographic image using the imaging system 18 according to the first exemplary embodiment.

The operational mode of the electronic cassette 32 in the state when the power is switched on (state on start up) is the initial state of a non-operational state (NOP state), and the electronic cassette 32 is operated based on instruction data received by wireless communication from the console 42.

However, when the power of the electronic cassette 32 is switched on the radiation detector 60 internally housed in the electronic cassette 32 (see FIG. 4) accumulates charge in each of the storage capacitors 68, due to dark current etc., even in a state in which X-rays are not irradiated thereon. The cassette control unit 92 therefore outputs an instruction signal instructing resetting to the signal processing unit 82 when the operational mode is the non-operational state. When the signal processing unit 82 is input with the instruction signal instructing resetting, the switch 84C (see FIG. 5) is switched on and both electrodes of the condenser 84B are shorted. The unwanted charge that has accumulated in the condenser 84B is discharged by shorting both electrodes of the condenser 84B in this manner.

When the console 42 can communicate with the electronic cassette 32, instruction data C1 instructing operation of the reset mode is transmitted to the electronic cassette 32 by wireless communication.

When the cassette control unit 92 receives the instruction data C1 instructing operation of the reset mode, the operational mode progresses to the reset mode, and after a specific accumulation period has elapsed, longer than the radiation duration of irradiation of radiation from the imaging device 34 when capturing a radiographic image, the gate line driver 80 is controlled, and an ON signal is output from the gate line driver 80 in sequence one line at a time to each of the gate lines 76, and charge extraction is performed in sequence one line at a time from each of the TFT's 70 connected to each of the gate lines 76. Charge that has accumulated in the storage capacitor 68 thereby flows as a charge signal out through each of the data lines 78. During periods in which the operational mode is the reset mode, after the accumulation period has elapsed the cassette control unit 92 outputs the ON signal to each of the gate lines 76, in sequence one line at a time, and repeats the accumulation extraction operation to reset one frame's worth by extracting charge accumulated in each of the respective pixel portions 74 of the radiation detector 60.

When radiation exposure condition instruction operation has been performed to the operation panel 102, the console 42 transmits radiation exposure condition data C2, of the tube voltage, tube current and irradiation period for X-ray irradiation instructed by the radiation exposure condition instruction operation, to the imaging device 34 via the communications cable 35. When capturing a radiographic image, the console 42 transmits imaging control data C3, of the radiation duration of irradiation of radiation from the imaging device 34 etc., to the electronic cassette 32 by wireless communication.

In the imaging device 34, when the power has been switched on and a specific initialization operation has been completed, the imaging device 34 is on standby with an operational state of a sleep state. When in receipt of the radiation exposure condition data C2 the imaging device 34 stores the received radiation exposure conditions and the operational state progresses to the drive state. When the operational state of the imaging device 34 has returned to the drive state, data C4, indicating that imaging preparation is complete, is transmitted to the console 42 via the communications cable 35.

On receipt of the imaging control data C3 the cassette control unit 92 of the electronic cassette 32 stores the received imaging control data.

On receipt of the data C4 indicating that imaging preparation is complete, the console 42 displays that imaging preparation is completed on the display 100, and imaging instruction operation of the operation panel 102, instructing imaging, is enabled. In the imaging system 18 according to the present exemplary embodiment, there are two stages of operation in the imaging instruction operation to the operation panel 102, and radiographic images are captured by performing the second stage of imaging instruction operation on the operation panel 102 after the first stage of imaging instruction operation has been performed. The two stages of imaging instruction operation may be, for example, by depressing two buttons of the operation panel 102 in sequence, or may be by partially depressing one button and then depressing it by the full amount.

When the first stage of imaging instruction operation is performed to the operation panel 102, the console 42 transmits instruction data C5 instructing radiation exposure preparation to the imaging device 34 via the communications cable 35.

When in receipt of the instruction data C5 instructing radiation exposure preparation, the imaging device 34 puts the radiation source 130 on standby to carry out radiation exposure with the tube voltage and tube current indicated in the radiation exposure conditions stored just previously. When the imaging device 34 has completed putting the radiation source 130 on standby, the imaging device 34 transmits instruction data C6 indicating standby completion to the console 42 via the communications cable 35.

On receipt of the instruction data C6 indicating standby completion, the console 42 enables the second stage of imaging instruction operation. When the second stage of imaging instruction operation is performed to the operation panel 102, the console 42 transmits request data C7 requesting the radiation irradiation possibility for imaging to the electronic cassette 32 by wireless communication.

However, the electronic cassette 32 according to the present invention is, as described above, performing repeated accumulation extraction operations after the accumulation period has elapsed to extract the charge that has accumulated in each of the respective pixel portions 74 of the radiation detector 60. This accumulation period is longer than the irradiation period of radiation irradiation when capturing a radiographic image. Therefore, a radiographic image can be taken straight away when the electronic cassette 32 can be irradiated with radiation of the irradiation period from the radiation source within the accumulation period of the accumulation extraction operation currently being carried out.

Therefore, when the cassette control unit 92 has received the request data C7 requesting the irradiation possibility, irradiation possibility determination processing is performed, and determination is made as to whether or not irradiation of radiation of the irradiation period from the radiation source is possible within the accumulation period of the accumulation extraction operation currently being carried out.

Figure 7:
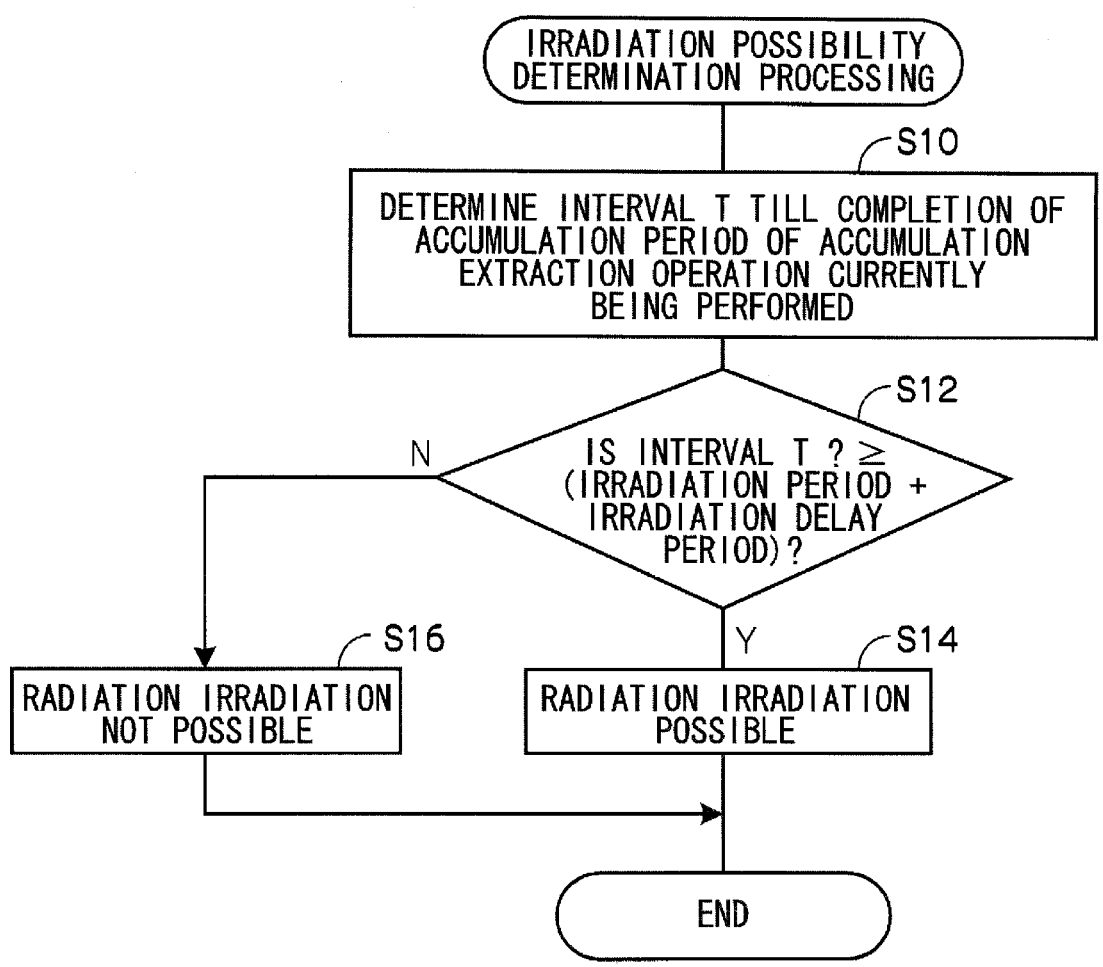
FIG. 7 is a flow chart showing the flow of irradiation possibility determination processing according to an exemplary embodiment.

FIG. 7 shows a flow of irradiation possibility determination processing executed by the cassette control unit 92.

In step S10 the interval T until completion of the accumulation period of the accumulation extraction operation currently being carried out is determined.

In the next step S12, determination is made as to whether or not the interval T determined in step S10 is the same as or greater than the summed duration of the irradiation period received as imaging control data C3 and a specific irradiation delay period. When the interval T is the same as or greater than the summed duration, the routine proceeds to step S14, and when the interval T is shorter than the summed duration the routine proceeds to step S16.

In the imaging system 18 according to the present exemplary embodiment, there is a time lag from when the imaging device 34 permits radiation irradiation of the electronic cassette 32 until the electronic cassette 32 is actually irradiated with radiation. Therefore, in the present exemplary embodiment, the interval from when permission is given to irradiate the electronic cassette 32 with radiation up to when radiation is actually irradiated is measured, by experimentation or the like, and an interval corresponding to from when permission is given to irradiate radiation up to when radiation is actually irradiated is determined as the irradiation delay period. There are occasions in wireless communication when the communications state becomes unstable, delaying data receipt. The irradiation delay period can be lengthened by taking into consideration a certain amount of delay. The communications state of wireless communication by the wireless communications unit 94 may also be detected, and the cassette control unit 92 may change the irradiation delay period lengthening according to the instability of the communications state. Preferably the accumulation period is made sufficiently longer than the irradiation period taking into consideration a certain amount of delay, and the cassette control unit 92 may change the lengthening of the accumulation period according to the instability of the communications state.

In the present exemplary embodiment, since the time lag from when radiation irradiation of the electronic cassette 32 is permitted until actual irradiation with radiation is taken into consideration, in order to determine whether or not radiation irradiation is possible determination is made as to whether or not the interval T is the same as or greater than the summed duration of the irradiation period and the irradiation delay period.

At step 14 determination is made that radiation irradiation is possible and processing is ended. At step 16 determination is made that radiation irradiation is not possible and processing is ended.

When the determined result of irradiation possibility determination processing is determination that radiation irradiation is possible, the cassette control unit 92 transmits instruction data C8 that permits the radiation irradiation and instructs imaging commencement, to the console 42 by wireless communication. When determination is made that irradiation is not possible then after the start of the accumulation period in the next accumulation extraction operation, the cassette control unit 92 sends the instruction data C8 that permits the radiation irradiation and instructs imaging commencement to the console 42 by wireless communication. When the instruction data C8 instructing imaging commencement has been sent by wireless communication to the console 42 the cassette control unit 92 moves from the operational mode to the imaging mode.

FIG. 6 shows a case in which the interval T up to the end of the accumulation period of the accumulation extraction operation currently being carried out is greater than the summed duration of the irradiation period and the irradiation delay period, and so determination is made that irradiation is possible, and the instruction data C8 instructing imaging commencement is transmitted during the accumulation period of the accumulation extraction operation currently being carried out.

Figure 8:
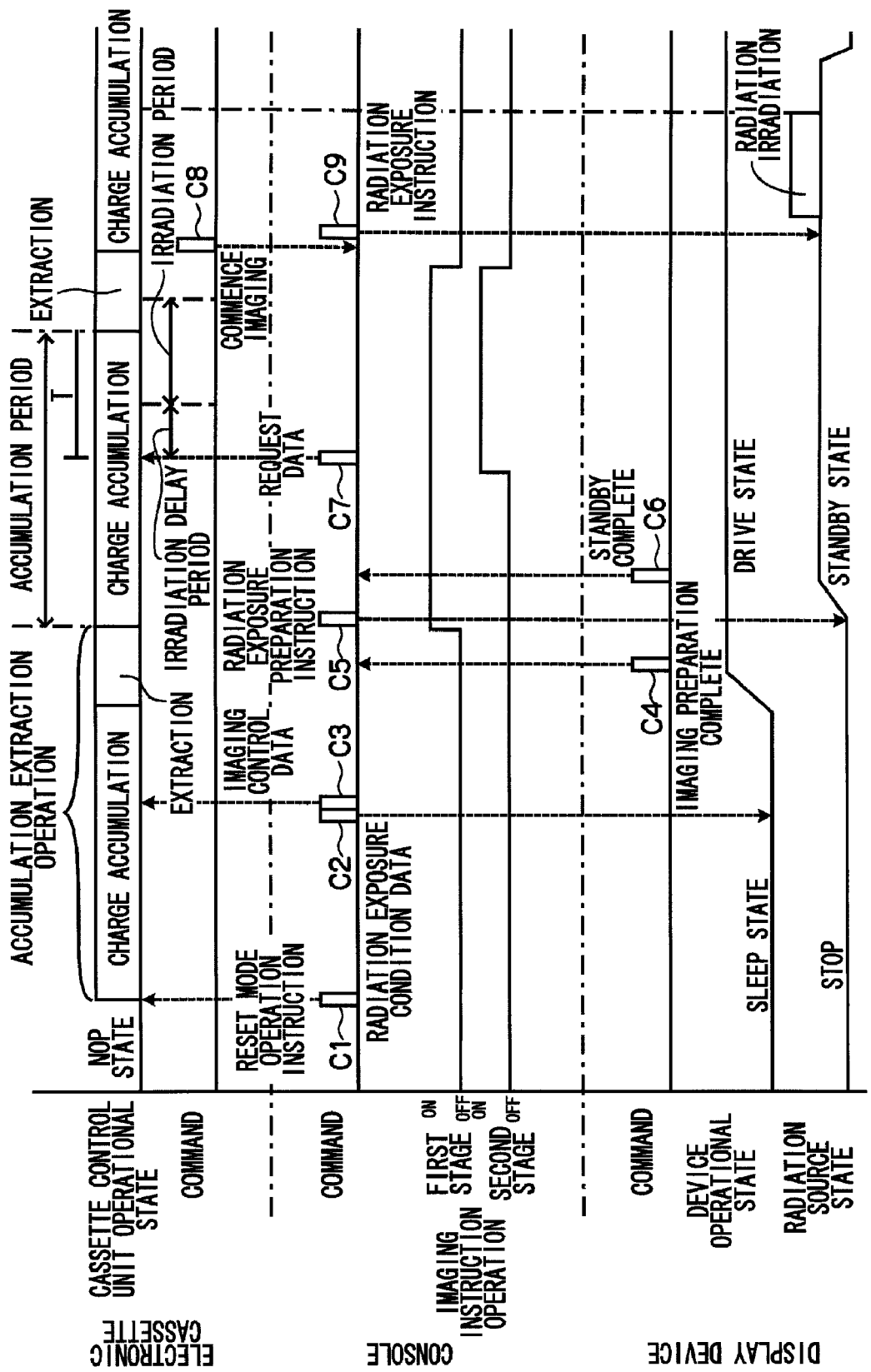
FIG. 8 is a timing chart showing the operation flow when capturing a radiographic image according to the first exemplary embodiment.

However, FIG. 8 shows a case in which the interval T up to the end of the accumulation period of the accumulation extraction operation currently being carried out is less than the summed duration of the irradiation period and the irradiation delay period, and so determination is made that irradiation is not possible, and the instruction data C8 instructing imaging commencement is transmitted after starting the accumulation period of the next accumulation extraction operation.

When in receipt of the instruction data C8 instructing imaging commencement, the console 42 transmits instruction data C9 instructing radiation exposure to the imaging device 34 via the communications cable 35.

When in receipt of the instruction data C9 instructing radiation exposure, the imaging device 34 irradiates X-rays from the radiation source 130 for the irradiation period given in the radiation exposure conditions that were stored just previously.

The X-rays irradiated from the radiation source 130 reach the electronic cassette 32 after passing through the patient 30. Charge is thereby accumulated in the storage capacitor 68 of each of the pixel portions 74 of the radiation detector 60 internally housed in the electronic cassette 32, in a charge amount according to the radiation amount of the irradiated X-rays.

Since the cassette control unit 92 repeatedly performs accumulation extraction operations, after the accumulation period has elapsed, the gate line driver 80 is controlled, such that an ON signal is output to each of the gate lines 76 in sequence one line at a time, and each of the TFT's 70 connected to each of the gate lines 76 is switched ON in sequence one line at a time.

In the radiation detector 60, when each of the TFT's 70 connected to each of the gate lines 76 has been switched ON in sequence one line at a time, charge that has been accumulated in the storage capacitor 68 flows out, as a charge signal, through each of the data lines 78 in sequence one line at a time. The charge signals flowing out through each of the data lines 78 are input to the individual sample-and-hold circuits 84 and converted into voltage signals, the converted voltage signals are input in sequence (serially) into the multiplexer 86, converted into digital image data by the A/D convertor 88 and stored in the memory 90.

When X-rays irradiation from the radiation source 130 has been completed, the console 42 transmits an image data transmission request signal to the electronic cassette 32 by wireless communication.

When in receipt of the image data transmission request signal, the cassette control unit 92 transmits image data stored in the memory 90 to the console 42, one frame's worth at a time.

However, even in the state in which X-rays are not being irradiated, charge is generated by dark current or the like, and charge is accumulated in the storage capacitors 68 of each of the pixel portions 74, this also generating noise in radiographic images obtained by imaging due to such charge generated by dark current or the like.

Therefore, in according to the present exemplary embodiment, the charge is extracted from each of the pixel portions 74 of the radiation detector 60 by the accumulation extraction operation when the electronic cassette 32 is in the un-irradiated state of the radiation detector 60, image data based on the charge amounts extracted is stored as data representing noise in the memory 90, and image data together with data representing noise is transmitted. In the present exemplary embodiment, the image data based on the charge amounts extracted by the accumulation extraction operation just after taking an radiographic image is used as the data representing noise. By deriving data representing noise in the accumulation extraction operation just after a radiographic image has been taken in this manner, noise data can be obtained that was generated in each of the pixel portions 74 of the radiation detector 60 in a state close to that during imaging. Note that repeated accumulation extraction operations are performed in the electronic cassette 32, and since the accumulation period of the accumulation extraction operations is the same each time, image data based on the charge amounts extracted in an accumulation extraction operation previous to that of a given radiographic image capture can be used as the data representing noise. When the data representing noise is obtained in an accumulation extraction operation prior to a radiographic image capture, since there is no requirement after imaging to obtain data representing noise, the process commencement of image processing to remove noise, described later, can be made earlier, and corrected radiographic images can be displayed early.

In the console 42, specific image processing is performed on transmitted image data, and image processing to remove noise is also performed using the data representing noise also transmitted with the image data. The image data after image processing is stored in the HDD 110 in a state associated with the patient information of the patient 30. The console 42 also outputs an image signal representing the radiographic image after image processing to the display device 36, and displays the image signal on the display unit 36A of the display device 36. A surgeon 26 proceeds with surgery while confirming the radiographic image that has been displayed on the display unit 36A.

It should be noted that during image processing the console 42 may output an image signal representing the radiographic image with the transmitted image data and a radiographic image prior to image processing may be displayed on the display unit 36A of the display device 36. By so doing, since the radiographic image can be displayed earlier after imaging, early confirmation of the imaging position etc. can be made.

According to the first exemplary embodiment, as described above, after the specific accumulation period has elapsed, being longer than the irradiation period for radiation irradiation when capturing a radiographic image, the radiation detector 60 is controlled so as to perform repeated accumulation extraction operations to extract charge that has accumulated in each of the respected pixel portions 74 of the radiation detector 60. When request data C7 requesting the irradiation possibility is received, determination is made as to whether or not radiation irradiation is possible of the irradiation period from the radiation source within the accumulation period of the accumulation extraction operation currently being carried out, and when irradiation is possible permission is given for radiation irradiation, and the time lag till radiographic image taking can be shortened. When irradiation is not possible, permission for radiation irradiation is given after commencing the accumulation period of the next accumulation extraction operation, therefore is no limitation to the timing of imaging, and radiographic images can be taken at specific timings.

According to the first exemplary embodiment, image processing is performed in which image data representing a radiographic image based on the charge amount extracted from each of the pixel portions 74 of the radiation detector 60 in an accumulation extraction operation when radiation has been irradiated onto the radiation detector 60, is corrected with data representing noise based on the charge amount extracted from each of the pixel portions 74 of the radiation detector 60 in an accumulation extraction operation when in a state in which radiation has not been irradiated to the radiation detector 60, a radiographic image can be obtained with noise, generated by dark current or the like, removed therefrom, even if the accumulation period is long.

Second Exemplary Embodiment

Explanation will now be given of a second exemplary embodiment of the present invention.

Since the configurations of a radiology information system 10 and a electronic cassette 32 of the second exemplary embodiment are the same as those of the first exemplary embodiment (see FIGS. 1 to 3), explanation thereof will be omitted.

Figure 9:
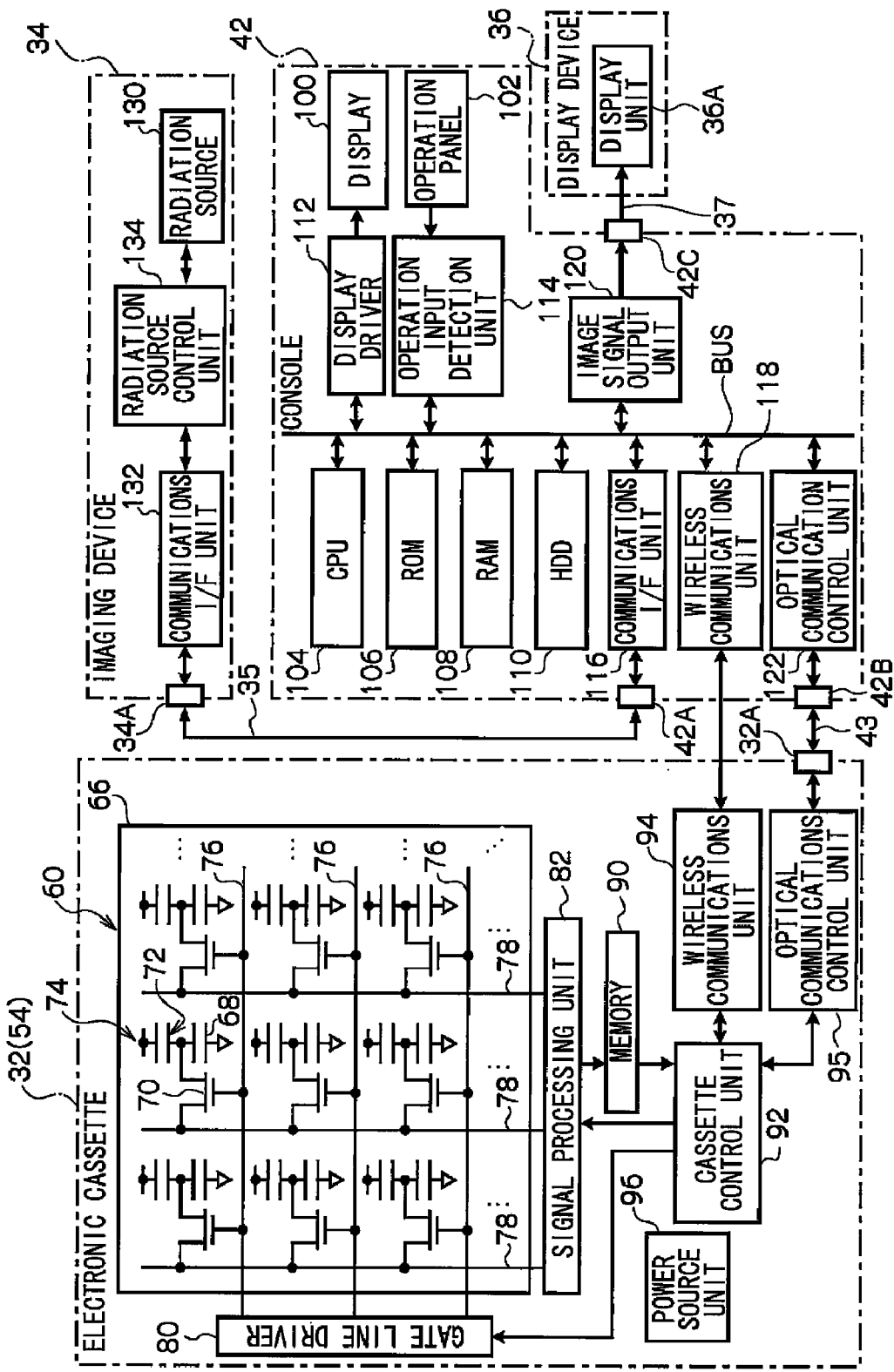
FIG. 9 is a block diagram showing a detailed configuration of a radiographic imaging system according to a second exemplary embodiment.

FIG. 9 shows a block diagram showing a detailed configuration of an imaging system 18 according to the second exemplary embodiment. Similar parts of the configuration to those of the above first exemplary embodiment (FIG. 4) are allocated the same reference numerals and explanation thereof is omitted.

In the imaging system 18 according to the present exemplary embodiment the electronic cassette 32 and a console 42 have communications capability for wired communication as well as for wireless communication.

The electronic cassette 32 is provided with a connection terminal 32A for communication with the console 42. The console 42 is provided with a connection terminal 42B for performing communication with the electronic cassette 32.

In the electronic cassette 32 a communications cable 43 is connected to the connection terminal 32A when capturing radiographic images, connecting the electronic cassette 32 to the console 42 via the communications cable 43. In the present exemplary embodiment, the since high speed data transmission is performed between the electronic cassette 32 and the console 42, an optical communications cable employing optical fibers is used for the communications cable 43, and data is transmitted by optical communication between the electronic cassette 32 and the console 42.

In the electronic cassette 32 an optical communication control unit 95 connected to the cassette control unit 92 and to the connection terminal 32A is also provided for controlling transmission of various data between the electronic cassette 32 and the console 42, via the connection terminal 32A and the communications cable 43. The cassette control unit 92 is capable of transmitting and receiving various data to and from the console 42 via the optical communication control unit 95.

The console 42 is further equipped with an optical communication control unit 122 that is connected to the connection terminal 42B, and that transmits and receives various data to and from the electronic cassette 32 via the connection terminal 42B and the communications cable 43. The optical communication control unit 122 is connected to a systems bus BUS. Consequently, the CPU 104 can control transmitting and receiving of various data with the electronic cassette 32 through the optical communication control unit 122.

The electronic cassette 32 and the console 42 in the present exemplary embodiment perform wired communication when connected together by the communications cable 43, and perform wireless communication when the communications cable 43 is not connected.

In wired communication the transmission speed of data is faster in comparison to wireless communication, and since the communications state is stable and there is no communication delay generated, the time lag from permitting radiation irradiation to the electronic cassette 32 and actual radiation irradiation is short.

According to the present exemplary embodiment, when performing wireless communication with the console 42 and the operational mode of the cassette control unit 92 becomes the reset mode, in a similar manner to in the first exemplary embodiment, after an accumulation period has elapsed, the cassette control unit 92 controls the radiation detector 60 so as to repeatedly perform an accumulation extraction operation to extract charge that has accumulated in each of the respective pixel portions 74 of the radiation detector 60.

However, when in wired communication with the console 42 the cassette control unit 92 controls the radiation detector 60 so as to repeatedly perform an extraction operation to extract charge that has accumulated in each of the respective pixel portions 74 of the radiation detector 60.

Figure 10:
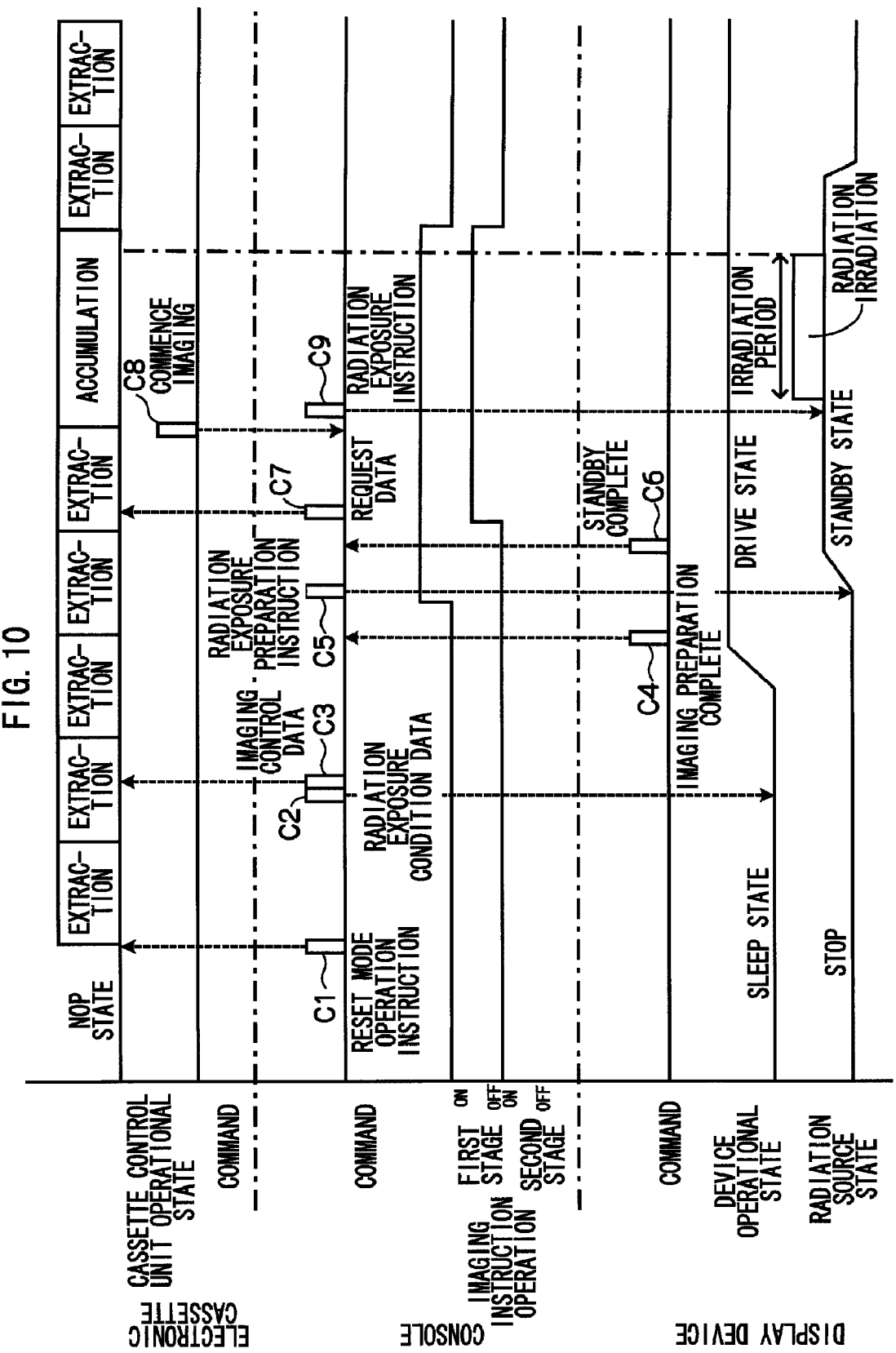
FIG. 10 is a timing chart showing the operation flow when capturing a radiographic image according to the second exemplary embodiment.

FIG. 10 shows a timing chart showing the operation flow when capturing a radiographic image when the electronic cassette 32 and the console 42 are performing wired communication. Similar parts of the configuration to those of the above first exemplary embodiment (FIG. 6) are allocated the same reference numerals and explanation thereof is omitted.

When in receipt of instruction data C1 instructing operation of the reset mode, the operational mode of the cassette control unit 92 moves to the reset mode, and the cassette control unit 92 controls the gate line driver 80 such that an ON signal is output from the gate line driver 80 to each of the gate lines 76, in sequence one line at a time, controlling such that the extraction operation is repeatedly performed by switching each of the TFT's 70 that are connected to each of the gate lines 76 ON in sequence one line at a time. The charge that has accumulated in each of the storage capacitors 68 thereby flows out through each of the data lines 78 as a charge signal for each time of extraction operation.

When radiation exposure condition instruction operation has been performed to the operation panel 102, the console 42 transmits radiation exposure condition data C2, of the tube voltage, tube current, and irradiation period etc. instructed in the radiation exposure condition instruction operation, to the imaging device 34 via the communications cable 35. When capturing a radiographic image, the console 42 transmits imaging control data C3, of the accumulation period for charge accumulation in the storage capacitor 68 of the radiation detector 60 etc., to the electronic cassette 32 through the communications cable 43.

When in receipt of radiation exposure condition data C2 the imaging device 34 stores the received radiation exposure condition data and also the operational state of the imaging device 34 moves to the drive state.

When in receipt of the imaging control data C3 the cassette control unit 92 of the electronic cassette 32 stores the received imaging control data.

When in receipt of request data C7 requesting the irradiation possibility, the cassette control unit 92 performs extraction operation until one frame's worth of extraction operation is complete, and after one frame's worth of extraction operation is completed the cassette control unit 92 transmits instruction data C8 instructing imaging commencement to the console 42 via the communications cable 35, and the operational mode of the cassette control unit 92 moves to the imaging mode.

When in receipt of the instruction data C8 instructing imaging commencement the console 42 transmits instruction data C9 instructing radiation exposure to the imaging device 34 via the communications cable 43.

When in receipt of the instruction data C9 instructing radiation exposure the imaging device 34 irradiates X-rays from the radiation source 130 for the irradiation period represented in the radiation exposure condition data stored just previously.

The X-rays irradiated from the radiation source 130 reach the electronic cassette 32 after passing through the patient 30. Charge is thereby accumulated in the storage capacitor 68 of each of the pixel portions 74 of the radiation detector 60 internally housed in the electronic cassette 32, in a charge amount according to the radiation amount of the irradiated X-rays.

After transmitting the instruction data C8 instructing imaging commencement, the cassette control unit 92, after standby of the accumulation period set in the imaging control data stored just previously, controls the gate line driver 80 so as to output from the gate line driver 80 an ON signal to each of the gate lines 76 in sequence one line at a time, and each of the TFT's 70 that are connected to the each of the gate lines 76 are switched ON in sequence one line at a time. The charge that has been accumulated in the storage capacitor 68 thereby flows out as a charge signal through each of the data lines 78 in sequence one line at a time. The charge signals flowing out through each of the data lines 78 are input into the individual sample-and-hold circuits 84 and converted into voltage signals, and the converted voltage signals are input in sequence (serially) to a multiplexer, converted into digital image data by an A/D convertor, and stored in the memory 90.

In the above manner, according to the second exemplary embodiment, since the time lag with wired communication is relatively short in comparison to wireless communication, only extraction operation is performed as the reset mode when the electronic cassette 32 and the console 42 are in wired communication, and rapidly captured radiographic images can be obtained by, after completing one frame's worth of extraction operation, transmitting the instruction data C8 instructing imaging commencement when request data C7 requesting the irradiation possibility is received.

It should be noted that while explanation has been given of cases in the above exemplary embodiments of application to an electronic cassette, which is a portable radiographic imaging device, the present invention is not limited thereto, and application may also be made to a non-portable radiographic imaging device.

Also, while explanation has been given in the above first exemplary embodiment of a case in which image processing is performed in the console 42 to remove noise by correcting image data representing radiographic images with data representing noise, the present invention is not limited thereto, and, for example, the above image processing may be performed in the cassette control unit 92 of the electronic cassette 32.

Also, while explanation has been given in the above second exemplary embodiment of a case in which, when the electronic cassette 32 and the console 42 are performing wired communication, only extraction operation is performed as the reset mode, and on receipt of the request data C7 requesting the irradiation possibility the instruction data C8 instructing imaging commencement is transmitted after completing one frame's worth of extraction operation, the present invention is however not limited thereto. For example, control may be performed in a similar manner to that when in wireless communication even when the electronic cassette 32 and the console 42 are performing wired communication. The time lag is relatively long with wireless communication in comparison with wired communication. Therefore, when wireless communication is performed the accumulation period is preferably made relatively long in comparison to when performing wired communication.

Also, while explanation has been given in the above second exemplary embodiment in FIG. 10 of a case in which the electronic cassette 32 only performs repeated extraction operations as the reset mode, the present invention is not limited thereto, and, for example, configuration may be made so that when the communications cable 43 connecting the electronic cassette 32 and the console 42 is pulled out and switch over is made to wireless communication, accumulation extraction operations are performed after completing the extraction operation currently in progress. In addition, configuration may be made so that when switch over is made to wired communication from wireless communication, extraction operations are performed after completing the accumulation extraction operation currently in progress.

Also, while explanation has been given in the above exemplary embodiments of examples of the configuration of the radiology information system 10 (see FIG. 1), the configuration of the imaging system 18 (see FIGS. 2, 4 and 9) and the configuration of the electronic cassette 32 (see FIG. 3), obviously various changes thereto are possible according to the circumstance, within a range not departing from the spirit of the present invention.

Also, while explanation has been given in each of the above exemplary embodiments of examples of the operation flow when capturing radiographic images (see FIGS. 6, 8 and 10), obviously various changes thereto are possible according to the circumstance, within a range not departing from the spirit of the present invention.

Also the flow of irradiation possibility determination processing explained in each of the above exemplary embodiments (see FIG. 7) is only an example, and obviously various changes thereto are possible according to the circumstance within a range not departing from the spirit of the present invention.

What is claimed is:

1. A radiographic imaging device comprising:
    a radiation detector that has a plurality of sensor portions that accumulate charge generated due to radiation being irradiated thereon when capturing a radiographic image;
    a receiving unit that receives request data requesting radiation irradiation permission from a control device that controls a radiation source for radiation irradiation when capturing a radiographic image;
    a control unit that controls the radiation detector such that an accumulation extraction operation is repeatedly performed that extracts charge that has accumulated in each of the plurality of sensor portions of the radiation detector, the accumulation extraction operation being performed after a specific accumulation period has elapsed, the specific accumulation period being greater than an irradiation period of radiation irradiation from the radiation source when capturing a radiographic image;
    a determination unit that, when the request data is received by the receiving unit, determines whether or not radiation irradiation of the irradiation period from the radiation source is possible within an accumulation period of an accumulation extraction operation currently being carried out under control of the control unit; and
    a permission unit that permits radiation irradiation if the determination unit has determined that irradiation is possible, and that permits radiographic imaging after starting an accumulation period of a next accumulation extraction operation if the determination unit has determined that irradiation is not possible.

2. The radiographic imaging device of claim 1, wherein the determination unit determines irradiation to be possible when an interval until completion of the accumulation period of the accumulation extraction operation currently being carried out is the same as or greater than a summed duration of the irradiation period and a specific irradiation delay period, and wherein the determination unit determines irradiation not to be possible when the interval until completion is shorter than the summed duration.

3. The radiographic imaging device of claim 2, wherein the irradiation delay period is equivalent to an interval from when radiation irradiation permission is given to when radiation is actually irradiated.

4. The radiographic imaging device of claim 2, further comprising an image processing unit that performs image processing that corrects image data representing a radiographic image, based on a charge amount extracted from each of the plurality of sensor portions of the radiation detector in an accumulation extraction operation performed when radiation has been irradiated onto the radiation detector, with data representing noise based on a charge amount extracted from each of the plurality of sensor portions of the radiation detector in an accumulation extraction operation performed when radiation has not yet been irradiated onto the radiation detector.

5. The radiographic imaging device of claim 4, wherein the image processing unit performs image processing that corrects image data representing a radiographic image with data representing noise based on charge amounts extracted in an accumulation extraction operation performed just after capturing the radiographic image.

6. The radiographic imaging device of claim 4, wherein the image processing unit performs image processing that corrects image data representing a radiographic image with data representing noise based on charge amounts extracted in an accumulation extraction operation performed before capturing the radiographic image.

7. The radiographic imaging device of claim 1, wherein
    the receiving unit is configured to communicate with the control device by wired communication or wireless communication;
    the control unit controls the radiation detector such that the accumulation extraction operation is repeatedly performed when the receiving unit is performing wireless communication and controls the radiation detector so that an extraction operation is repeatedly performed that extracts the charge that has accumulated in each of the plurality of sensor portions of the radiation detector when the receiving unit is performing wired communication; and
    when the receiving unit is performing wired communication, the permission unit gives permission for radiation irradiation after the extraction operation currently being carried out is completed.

8. The radiographic imaging device of claim 1, wherein
    the receiving unit is able to communicate with the control device by wired communication or wireless communication; and
    the control unit sets the accumulation period relatively longer when the receiving unit is performing wireless communication than when performing wired communication.

9. The radiographic imaging device of claim 1, further comprising a display unit that displays a radiographic image represented by image data prior to performing image processing by an image processing unit.

* * * * *